(12) United States Patent
Eddy et al.

(10) Patent No.: US 9,603,924 B2
(45) Date of Patent: *Mar. 28, 2017

(54) BOVINE VIRUS VACCINES THAT ARE LIQUID STABLE

(71) Applicants: INTERVET INTERNATIONAL B.V., Boxmeer (NL); INTERVET INC., Summit, NJ (US)

(72) Inventors: Brad Eddy, Omaha, NE (US); Zhisong Qiao, Omaha, NE (US); Kevin O'Connell, Omaha, NE (US)

(73) Assignee: Intervet Inc., Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/775,003

(22) PCT Filed: Mar. 14, 2014

(86) PCT No.: PCT/EP2014/055053
§ 371 (c)(1),
(2) Date: Sep. 11, 2015

(87) PCT Pub. No.: WO2014/140239
PCT Pub. Date: Sep. 18, 2014

(65) Prior Publication Data
US 2016/0030556 A1    Feb. 4, 2016

Related U.S. Application Data

(60) Provisional application No. 61/788,982, filed on Mar. 15, 2013.

(51) Int. Cl.
| | | |
|---|---|---|
| *A61K 39/39* | (2006.01) | |
| *A61K 39/155* | (2006.01) | |
| *C12N 7/00* | (2006.01) | |
| *A61K 39/215* | (2006.01) | |
| *A61K 39/265* | (2006.01) | |
| *A61K 39/102* | (2006.01) | |
| *A61K 39/02* | (2006.01) | |
| *A61K 39/12* | (2006.01) | |
| *A61K 39/245* | (2006.01) | |
| *A61K 47/26* | (2006.01) | |
| *A61K 47/18* | (2017.01) | |
| *A61K 39/00* | (2006.01) | |

(52) U.S. Cl.
CPC ............. *A61K 39/39* (2013.01); *A61K 39/02* (2013.01); *A61K 39/0208* (2013.01); *A61K 39/102* (2013.01); *A61K 39/12* (2013.01); *A61K 39/155* (2013.01); *A61K 39/215* (2013.01); *A61K 39/245* (2013.01); *A61K 39/265* (2013.01); *A61K 47/183* (2013.01); *A61K 47/26* (2013.01); *C12N 7/00* (2013.01); *A61K 2039/5254* (2013.01); *A61K 2039/552* (2013.01); *A61K 2039/55583* (2013.01); *A61K 2039/70* (2013.01); *C12N 2710/16734* (2013.01); *C12N 2760/12234* (2013.01); *C12N 2760/18034* (2013.01); *C12N 2760/18634* (2013.01); *C12N 2770/20034* (2013.01); *C12N 2770/24333* (2013.01); *C12N 2770/24334* (2013.01)

(58) Field of Classification Search
None
See application file for complete search history.

(56) References Cited

U.S. PATENT DOCUMENTS

| | | |
|---|---|---|
| 3,155,589 A | 11/1964 | Slater et al. |
| 4,337,242 A | 6/1982 | Markus et al. |
| 4,451,569 A | 5/1984 | Kobayashi et al. |
| 5,443,959 A | 8/1995 | Kikuchi et al. |
| 5,565,318 A | 10/1996 | Walker et al. |
| 5,593,824 A | 1/1997 | Tremi et al. |
| 5,763,409 A | 6/1998 | Bayol et al. |
| 5,932,223 A | 8/1999 | Burke et al. |
| 6,039,958 A | 3/2000 | Koyama et al. |
| 6,231,860 B1 | 5/2001 | Fanget et al. |
| 6,331,303 B1 | 12/2001 | Briggs et al. |
| 6,931,888 B2 | 8/2005 | Shekunov et al. |
| 7,073,349 B2 | 7/2006 | Shekunov et al. |
| 7,351,416 B2 | 4/2008 | Briggs et al. |
| 7,959,929 B2 | 6/2011 | Crawford et al. |
| 8,192,747 B2 | 6/2012 | Vande Velde |
| 8,980,610 B2 | 3/2015 | Selvitelli et al. |
| 9,393,298 B2 * | 7/2016 | Buchanan ............ A61K 39/155 |
| 2003/0114482 A1 | 6/2003 | Pacifici et al. |
| 2004/0038878 A1 | 2/2004 | Tanikawa et al. |
| 2004/0154317 A1 | 8/2004 | Shekunov et al. |
| 2005/0178020 A1 | 8/2005 | Shekunov et al. |

(Continued)

FOREIGN PATENT DOCUMENTS

| | | |
|---|---|---|
| EP | 0028563 A1 | 5/1981 |
| EP | 0650734 | 10/1993 |

(Continued)

OTHER PUBLICATIONS

Saif ("Bovine respiratory coronavirus." Veterinary Clinics of North America: Food Animal Practice 26.2 (2010): 349-364).*
Medi (European Pharmaceutical Review. 2014; 19 (1): 16-20).*
Morefield (The AAPS Journal. Jun. 2011; 13 (2): 191-200).*
PCT International Search Report, for corresponding PCT Application No. PCT/EP2014/055053 mailed on Jun. 11, 2014, WO 2014/140239.
Arakawa, et al., Biotechnology applications of amino acids in protein purification and formulations, Amino Acids, 2007, 587-605, 33.

(Continued)

*Primary Examiner* — Shanon A Foley

(57) ABSTRACT

The present invention discloses liquid stable bovine vaccines that comprise a live attenuated virus, and a sugar alcohol. The present invention also discloses the manufacture of such vaccines and methods of protecting an animal by administration of such vaccines.

20 Claims, No Drawings

(56) References Cited

U.S. PATENT DOCUMENTS

| | | |
|---|---|---|
| 2007/0148765 A1 | 6/2007 | Evans et al. |
| 2007/0161085 A1 | 7/2007 | Trager et al. |
| 2007/0190163 A1 | 8/2007 | Malaknov et al. |
| 2007/0259348 A1 | 11/2007 | Phadke et al. |
| 2008/0226680 A1* | 9/2008 | Cravens ............... A61K 9/0043 424/278.1 |
| 2008/0248551 A1* | 10/2008 | Stinchcomb ........... A61K 39/12 435/236 |
| 2009/0010955 A1 | 1/2009 | Kapil et al. |
| 2009/0274734 A1 | 11/2009 | Daamen et al. |
| 2010/0015180 A1 | 1/2010 | Francon et al. |
| 2010/0124557 A1 | 5/2010 | Oberreither et al. |
| 2010/0196420 A1 | 8/2010 | Kapil |
| 2010/0297231 A1 | 11/2010 | Vehring et al. |
| 2011/0081380 A1 | 4/2011 | Francon et al. |
| 2012/0213810 A1 | 8/2012 | Burgard et al. |
| 2014/0056942 A1 | 2/2014 | Qiao et al. |

FOREIGN PATENT DOCUMENTS

| | | |
|---|---|---|
| EP | 1123710 A1 | 8/2001 |
| GB | 1575155 | 9/1980 |
| JP | 61053227 | 3/1986 |
| WO | 8906973 A1 | 8/1989 |
| WO | 03087327 A2 | 10/2003 |
| WO | 2004/017990 A1 | 3/2004 |
| WO | 2007035455 A2 | 3/2007 |
| WO | 2009092703 A1 | 7/2009 |
| WO | 2010125084 A1 | 11/2010 |
| WO | 2010125087 A1 | 11/2010 |
| WO | 2011072218 | 6/2011 |
| WO | 2014009328 A1 | 1/2014 |
| WO | 2014029702 A1 | 2/2014 |
| WO | 2014140239 A1 | 9/2014 |
| WO | 2015044337 A2 | 4/2015 |
| WO | 2015121463 A2 | 8/2015 |
| WO | 2015124594 A1 | 8/2015 |

OTHER PUBLICATIONS

Ausar, et al., Analysis of the Thermal and pH Stability of Human Respiratory Syncytial Virus, Molecular Pharmaceutics, 2005, 491-499, 2-6.

Ausar, et al., High-throughput Screening of Stabilizers for Respiratory Syncytial Virus, Human Vaccines, 2007, 68-77, 3-3.

Brandau, et al., Thermal Stability of Vaccines, Journal of Pharmaceutical Sciences, 2003, 218-231, 92-2.

Chen, et al., Opportunities and challenges of developing thermostable vaccines, Expert Reviews, 2009, 547-557, 8-5.

Kamerzell, et al., Protein-excipient interactions: Mechanisms and biophysical characterization applied to protein formulation development, Advanced Drug Delivery Reviews, 2011, 1118-1159, 63.

Patel, et al., Stability Consideration for Biopharmaceuticals, Part 1, BioProcess Technical, 2011, 1-10.

Burke, Carl J., Formulation, Stability, and Delivery of Live Attenuated Vaccines for Human Use, Critical Reviews in Therapeutic Drug Carrier Systems, 1999, 1-83, 16(1).

Cavanagh, et al., Coronavirus avian infectious bronchitis virus, Veterinary Research, 2007, pp. 281-297.

Chokephaibulkit et al., Challenges for the formulation of a universal vaccine against dengue, Experimental Biology and Medicine, 2013, pp. 566-578, 238.

Crawford, et al., Transmission of Equine Influenza Virus to Dogs, Science, 2005, 482-485, 310, US.

Derwent; English Abstract of JP61053227; Title: Mixed live vaccine for Japanese encephalitis and swine parvovirus infection; Sasaki; Mar. 17, 1986.

Ellingson, et al., Vaccine efficacy of porcine reproductive and respiratory Syndrome Virus Chimeras, Vaccine, 2010, pp. 2679-2686, 28.

International Search Report for corresponding PCT International Application No. PCT/EP2013/064422, mailed on Oct. 2, 2013, 5 Pages.

International Search Report for PCT/EP2014/070608, mailed on May 11, 2015.

International Search report for PCT/EP2015/053188 dated Aug. 12, 2015, 16 pages.

International Search report for PCT/EP2015/053364 dated Aug. 12, 2015, 16 pages.

Intervet UK Ltd., The UK's Favourite Small Animal Vaccines; the Nobivac Range, Nobivac, The Future of Vaccination, 2006, XP002714516; 1-48, 1.

Mochizuki, Masami, Growth characteristics of canine pathogenic viruses in MDCK cells cultured in RPMI 1640 medium without animal protein, Vaccine, 2006, pp. 1744-1748, 24.

Papatsiros, Porcine Respiratory and Reproduction Syndrome Virus Vaccinology: A Review for Commercial Vaccines, American Journal of Animal and Veterinary Sciens, 2012, pp. 149-158, 7-4.

PCT International Search Report for corresponding PCT Application No. PCT/EP2013/067169, mailed on Oct. 25, 2013 (4 pages).

Schering-Plough Animal Health Ltd., Nobivac DHPPi; Combined Live Attenuated Freeze-Dried Canine Distemper Virus, Adenovirus Type 2, Parvovirus and Parainfluenza Virus Vaccine, Restricted Veterinary Medicine, 2013, XP002714517; 1-2, 1.

Schlehuber, et al., Towards Ambient Temperature-stable vaccines: The identification of thermally stabilizing liquid formulations for measles virus using an innovative high-throughput infectivity assay, Vaccine, 2011, pp. 5031-5039, 29.

Taguchi, et al., Antibody titers for canine parvovirus type-2, canine distemper virus, and canine adenovirus type-1 in adult household dogs, Canine Veterinary Journal, 2011, 983-986, 52.

* cited by examiner

US 9,603,924 B2

BOVINE VIRUS VACCINES THAT ARE LIQUID STABLE

CROSS-REFERENCE TO RELATED APPLICATIONS

This application is a national stage entry under 35 U.S.C. §371 of PCT/EP2014/055053, filed on Mar. 14, 2014, which claims priority under 35 U.S.C. §119(e) to provisional application U.S. Ser. No. 61/788,982, filed on Mar. 15, 2013, the contents of both of which are hereby incorporated by reference in their entireties.

FIELD OF THE INVENTION

The present invention pertains to liquid stable bovine vaccines that comprise a live attenuated bovine virus. The invention also pertains to the manufacture of such vaccines and methods of vaccinating animal subjects.

BACKGROUND

There are a significant number of viruses that can infect cattle. Such viruses include bovine viral diarrhea virus types 1 and 2, (BVDV1, or alternatively BVD1; and BVDV2, or alternatively BVD2), infectious bovine rinotracheitis (IBR) virus, parainfluenza type 3 (PI3), bovine respiratory syncytial virus (BRSV), Rift Valley fever virus (RVFV), and bovine respiratory coronavirus (BRCV). In addition, there are a number of bacteria that can infect cattle too, including *Pasteurella multocida, Mannheimia haemolytica, Histophilus somni*, and *Mycoplasma bovis*.

It is now widely accepted that the best way of preventing disease due to bacterial or virus infections in bovine is to vaccinate them against these viruses. Moreover, multivalent live attenuated virus or bacterial vaccines can be safely administered that limit the number of vaccine injections required. Accordingly, there are commercially available multivalent live virus vaccines that protect against BVDV1 and BVDV2, IBR, PI3, and/or BRSV. However, heretofore, attenuated cattle viruses have been unstable when stored in liquid solutions. Therefore, most live attenuated bovine virus vaccines are lyophilized, i.e., freeze-dried, prior to their long-term storage. The live attenuated bovine virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized bovine vaccines that comprise live attenuated viruses are stored with augmented titers. However, such increased titers can lead to significant adverse events should the lyophilization process actually lead to less loss of activity than anticipated. Therefore, great care is required to formulate a vaccine to contain a virus titer that is not only safely below the amount that leads to adverse events, but that also maintains sufficient efficacy in view of the virus titer loss due to lyophilisation and subsequent storage.

Furthermore, there is a limitation to the size of a lyophilisation vials and/or number of doses contained within such vials due to relatively small standard stopper sizes for the tops of these vials. Therefore, large volumes of liquid become difficult to sublimate through the relatively small openings. In addition, a large vial requires that the user to somehow transfer a large volume of diluent to the lyophilized cake in a sterile manner, whereas the rehydration of many more smaller vials is just inconvenient. Indeed, either alternative is particularly vexing in a feedlot environment where the vaccine recipients, e.g., the cattle, reside. Therefore, there is a need for new live attenuated bovine virus vaccines that can reliably retain their virus titers at a safe and efficacious level.

The citation of any reference herein should not be construed as an admission that such reference is available as "prior art" to the instant application.

SUMMARY OF THE INVENTION

In order to overcome the deficiencies of current vaccines, the present invention provides novel liquid stable, live, attenuated bovine virus vaccines, as well as their corresponding immunogenic compositions. The liquid stable, live, bovine virus vaccines of the present invention can remain efficacious for extended periods such as 9 months or longer (e.g., about 1 to up to 3 years). The present invention also provides methods of administering such vaccines to an animal. The present invention further provides methods of preventing a disease in an animal through administering a vaccine of the present invention.

Accordingly, the present invention provides liquid stable vaccines that comprise a live attenuated virus, including multivalent vaccines that comprise a live virus. In certain embodiments the live virus is an attenuated virus. In other embodiments the live virus is a recombinant virus. In particular embodiments the live virus is both attenuated and recombinant. Recombinant viruses of the present invention can also encode a heterogeneous protein. In particular embodiments of this type, the heterogeneous protein is a virus, parasite or bacterial antigen.

In particular embodiments, the vaccine comprises a sugar additive that is a sugar alcohol. In certain embodiments the vaccine further comprises an amino acid. In particular embodiments the vaccine comprises 5 to 40% (w/v) of a sugar alcohol. In certain embodiments, the vaccine comprises 10 to 30% (w/v) of a sugar alcohol. In particular embodiments, the vaccine comprises 15 to 25% (w/v) of a sugar alcohol. In related embodiments the vaccine comprises 10 to 20% (w/v) of a sugar alcohol. In other embodiments, the vaccine comprises 20 to 25% (w/v) of a sugar alcohol. In more particular embodiments, the vaccine comprises 12 to 18% (w/v) of a sugar alcohol. In even more particular embodiments, the vaccine comprises about 15% (w/v) of a sugar alcohol. In related embodiments, the vaccine comprises about 23% (w/v) of a sugar alcohol. In certain embodiments, the liquid stable virus vaccines of the present invention comprise two or more sugar alcohols, with the total amount of the sugar alcohol in the liquid stable vaccines being 5-40% (w/v). In related embodiments, the liquid stable virus vaccines comprise two or more sugar alcohols, with the total amount of the sugar alcohol in the liquid stable vaccines being 10-30% (w/v).

In particular embodiments of the liquid stable virus vaccines of the present invention the sugar alcohol is sorbitol. In an alternative embodiment of this type, the sugar additive is mannitol. In related embodiments, the liquid stable vaccines further comprise a sugar additive that is a non-alcohol sugar, wherein the total amount of the sugar alcohol and the non-alcohol sugar in the liquid stable vaccine is 10-40% (w/v). In related embodiments the vaccine comprises 10-25% (w/v) of a sugar alcohol and 5-20% (w/v) of a non-alcohol sugar. In more particular embodiments the vaccine comprises 10-20% (w/v) of a sugar alcohol and 7.5-15% (w/v) of a non-alcohol sugar. In one such embodiment, the non-alcohol sugar, sugar additive is trehalose. In still other embodiments, the non-alcohol sugar, sugar additive is dextrose. In still other embodiments, the non-alcohol sugar, sugar additive is sucrose. In a particular embodiment of this type, the sugar additive is a combination of sucrose (non-alcohol sugar) and sorbitol (sugar alcohol). In a more particular embodiment of this type, the sugar additive is a combination of 10-20% sorbitol and 5-15% sucrose. In an even more particular embodiment of this type, the sugar additive is a combination of 15% sorbitol and 10% sucrose. In particular embodiments the non-alcohol sugar, sugar additive is actually a combination of two or more non-alcohol sugar, sugar additives.

The liquid stable vaccines of the present invention can range in pH from pH 6.0 to pH 8.0. In certain embodiments the pH range is from pH 6.5 to pH 7.8. In particular embodiments the pH range is from pH 6.8 to pH 7.5. In more particular embodiments the pH range is from pH 7.0 to pH 7.4. In an even more particular embodiment the pH is 7.2.

The liquid stable vaccines of the present invention can comprise a buffer. In a particular embodiment of this type, the buffer comprises 2.5 to 50 mM phosphate, e.g., sodium phosphate (NaPHOS) or potassium phosphate (KPHOS). In a related embodiment, the buffer comprises 5 to 25 mM phosphate. In particular embodiments, the buffer comprises 10 to 20 mM phosphate.

In yet other embodiments the buffer (i.e., the buffer solution) can comprise 0.15 to 0.75 M arginine. In particular embodiments the buffer comprises 2.5 to 50 mM phosphate and 0.15 to 0.75 M arginine. In more particular embodiments the buffer comprises 5 to 25 mM phosphate and 0.15 to 0.75 M arginine. In still more particular embodiments the buffer comprises 10 to 20 mM phosphate and 0.3 to 0.5 M arginine. In other embodiments the buffer comprises 2.5 to 50 mM phosphate. In a related embodiment, the buffer comprises 5 to 25 mM Tris. In particular embodiments, the buffer comprises 10 to 20 mM Tris. In related embodiments the Tris buffer comprises histidine.

The liquid stable vaccines of the present invention can comprise an amino acid. In certain embodiments as detailed above, the amino acid is arginine. In other embodiments, the amino acid is methionine. In still other embodiments, the amino acid is glycine. In yet other embodiments, the amino acid is glutamic acid. In related embodiments, the liquid stable vaccines comprise both arginine and methionine. In other embodiments, the liquid stable vaccines comprise both arginine and glycine. In yet other embodiments, the liquid stable vaccines comprise both glycine and methionine. In related embodiments, the liquid stable vaccines comprise both glutamic acid and methionine. In other embodiments, the liquid stable vaccines comprise both glutamic acid and glycine. In yet other embodiments, the liquid stable vaccines comprise both glutamic acid and arginine.

In related embodiments, the liquid stable vaccines comprise arginine, glutamic acid, and methionine. In other embodiments, the liquid stable vaccines comprise arginine, glutamic acid, and glycine. In yet other embodiments, the liquid stable vaccines comprise arginine, glutamic acid, and methionine. In still other embodiments, the liquid stable vaccines comprise arginine, glycine, and methionine. In yet other embodiments, the liquid stable vaccines comprise arginine, glycine, and methionine. In particular embodiments, the liquid stable vaccines comprise arginine, glycine, methionine, and glutamic acid.

In particular embodiments the final concentration of arginine, or glutamic acid, or glycine in the liquid stable vaccine is 0.15 to 0.75 M. In related embodiments, the final concentration of arginine, or glutamic acid, or glycine in the liquid stable vaccine is 0.25 to 0.75 M. In more particular embodiments, the final concentration of arginine, or glutamic acid, or glycine in the liquid stable vaccine is 0.2 to 0.6 M. In more particular embodiments, the final concentration of arginine, or glutamic acid, or glycine in the liquid stable vaccine is 0.2 to 0.5 M. In still other embodiments, the final concentration of arginine, or glutamic acid, or glycine in the liquid stable vaccine is 0.25 to 0.45 M.

In even more particular embodiments, the final concentration of arginine, or glutamic acid, or glycine in the liquid stable vaccine is about 0.45 M. In other particular embodiments, the final concentration of arginine, or glutamic acid, or glycine in the liquid stable vaccine is about 0.3 M.

In particular embodiments the final combined concentration of arginine together with glutamic acid and/or glycine in the liquid stable vaccine is 0.15 to 0.75 M. In related embodiments, the final concentration of arginine together with glutamic acid and/or glycine in the liquid stable vaccine is 0.25 to 0.75 M. In other embodiments, the final combined concentration of arginine together with glutamic acid and/or glycine in the liquid stable vaccine is 0.2 to 0.6 M. In more particular embodiments, the final combined concentration of arginine together with glutamic acid and/or glycine in the liquid stable vaccine is 0.3 to 0.5 M. In still other embodiments, the final concentration of arginine and glutamic acid, or glycine in the liquid stable vaccine is 0.25 to 0.45 M.

In even more particular embodiments, the final combined concentration of arginine together with glutamic acid and/or glycine in the liquid stable vaccine is about 0.45 M. In other particular embodiments, the final concentration of arginine together with glutamic acid and/or glycine in the liquid stable vaccine is about 0.3 M.

In particular embodiments the final concentration of methionine in the liquid stable vaccine is 0.025 to 0.3 M. In related embodiments, the final concentration of methionine in the liquid stable vaccine is 0.04 to 0.15 M. In more particular embodiments, the final concentration of methionine in the liquid stable vaccine is 0.06 to 0.09 M. In even more particular embodiments, the final concentration of methionine in the liquid stable vaccine is about 0.07 M.

The liquid stable vaccines of the present invention also can comprise a stabilizer protein. The stabilizer protein can be an intact protein and/or a protein hydrolysate. In particular embodiments the stabilizer protein is gelatin. In more particular embodiments the stabilizer protein contained by the liquid stable vaccine of the present invention is 0.4 to 1.6% gelatin. In alternative embodiments the stabilizer protein is a hydrolysate of whole casein. In particular embodiments of this type the stabilizer protein contained by the liquid stable vaccine of the present invention is 0.5-2.0% of a hydrolysate of whole casein. In certain embodiments the hydrolysate of whole casein is a proteolytic hydrolysate of whole casein. In yet other embodiments, the stabilizer protein contained by the liquid stable vaccine of the present invention is lactoglobulin or a lactalbumin hydrolysate.

In addition, the liquid stable vaccines of the present invention can also further comprise a chelating agent. Such chelating agents can include, but are not limited to: ethylenediaminetetraacetic acid (EDTA), citrate, 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS). The concentration of such chelating agents in the liquid vaccines of the present invention can vary from about 50 µM to 10 mM.

In particular embodiments the chelating agent is ethylenediaminetetraacetic acid (EDTA). In certain embodiments of this type the liquid stable vaccine comprises 0.050 to 1 mM EDTA. In particular embodiments the liquid stable vaccine comprises 0.25 to 0.75 mM EDTA. In more particular embodiments the liquid stable vaccine comprises about 0.5 mM EDTA.

In certain embodiments the liquid stable vaccines of the present invention can further comprise one or more free radical scavengers and/or antioxidants as a component. In a particular embodiment of this type a vaccine of the present invention comprises ascorbic acid. In a particular embodiment of this type the liquid stable vaccine comprises about 0.5 mM ascorbic acid. In a related embodiment the vaccine comprises alpha-tocopherol. In a particular embodiment of this type the liquid stable vaccine comprises about 0.5 mM alpha-tocopherol. In yet another embodiment, the vaccine comprises glutathione. In a particular embodiment of this type the liquid stable vaccine comprises about 3 mM glutathione. In still another embodiment, the vaccine comprises both alpha-tocopherol and ascorbic acid. In yet another embodiment the vaccine comprises both alpha-tocopherol and glutathione. In still another embodiment, the vaccine comprises both glutathione and ascorbic acid. In yet another embodiment the vaccine comprises ascorbic acid, alpha-tocopherol, and glutathione.

In related embodiments, the liquid stable vaccines of the present invention are maintained in sealed containers. In particular embodiments of this type, the liquid stable vaccines of the present invention are maintained in sealed containers that have an inert gas such as argon, nitrogen, or helium, above the liquid (e.g., have been back-filled with the inert gas).

The liquid stable vaccines of the present invention can further comprise an adjuvant. In particular embodiments of this type, the adjuvant is aluminum phosphate. In other such embodiments, the adjuvant is aluminum hydroxide. In still other embodiments, the adjuvant is a low molecular weight copolymer adjuvant which can form cross-linkage in solution to become a high molecular weight gel. In yet other embodiments, the adjuvant is made up of gel particles of sodium acrylate in water. In still other embodiments the adjuvant is a combination of two or more such adjuvants.

In particular embodiments the liquid stable vaccines of the present invention can further comprise a detergent and/or surfactant. In a certain embodiments of this type the surfactant is a polyoxyethylene-polyoxypropylene block copolymer. In a particular embodiment of this type the liquid stable vaccine comprises about 0.01% polyoxyethylene-polyoxypropylene block copolymer. In a specific embodiment of this type the polyoxyethylene-polyoxypropylene block copolymer is PLURONIC®F-68.

The liquid stable vaccines of the present invention can comprise a live attenuated bovine virus. In certain embodiments the live attenuated bovine virus is infectious bovine rinotracheitis (IBR) virus. In other embodiments the live attenuated bovine virus is bovine viral diarrhea type 1 virus (BVDV1). In yet embodiments the live attenuated bovine virus is bovine viral diarrhea type 2 virus (BVDV2). In still other embodiments the live attenuated bovine virus is parainfluenza type 3 (PI3) virus. In yet other embodiments the live attenuated bovine virus is bovine respiratory syncytial virus (BRSV). In still other embodiments the live attenuated bovine virus is bovine respiratory coronavirus (BRCV). In yet other embodiments the live attenuated bovine virus is a Rift Valley fever virus (RVFV).

In addition, the present invention provides liquid stable vaccines that are multivalent vaccines. The multivalent vaccines of the present invention can contain any combination of bovine viruses. In certain embodiments the multivalent vaccines of the present invention comprise both killed bovine viruses and live attenuated bovine viruses. In a particular embodiment of this type, the multivalent vaccine comprises killed BVDV1, killed BVDV2, and killed IBR, together with live attenuated PI3 and live attenuated BRSV. In a related embodiment, the multivalent vaccine comprises killed BVDV1, killed BVDV2, and killed IBR, together with live attenuated PI3, live attenuated BRSV, and live attenuated BRCV.

In other embodiments the multivalent vaccines of the present invention comprise only live attenuated bovine viruses. In particular embodiments, the multivalent vaccine comprises live attenuated BVDV1 and live attenuated BVDV2. In other embodiments, the multivalent vaccine comprises live attenuated BVDV1 and IBR. In still other embodiments, the multivalent vaccine comprises live attenuated BVDV1 and PI3. In yet other embodiments, the multivalent vaccine comprises live attenuated BVDV1 and live attenuated BRSV. In still other embodiments, the multivalent vaccine comprises live attenuated BVDV1 and live attenuated BRCV. In other embodiments, the multivalent vaccine comprises live attenuated BVDV2 and live attenuated IBR. In still other embodiments, the multivalent vaccine comprises live attenuated BVDV2 and live attenuated PI3. In yet other embodiments, the multivalent vaccine comprises live attenuated BVDV2 and live attenuated BRSV. In still other embodiments, the multivalent vaccine comprises live attenuated BVDV2 and live attenuated BRCV. In yet other embodiments, the multivalent vaccine comprises live attenuated IBR and live attenuated PI3. In still other embodiments, the multivalent vaccine comprises live attenuated IBR and live attenuated BRSV. In yet other embodiments, the multivalent vaccine comprises live attenuated IBR and live attenuated BRCV. In yet other embodiments, the multivalent vaccine comprises live attenuated PI3 and live attenuated BRSV. In still other embodiments, the multivalent vaccine comprises live attenuated PI3 and live attenuated BRCV. In yet other embodiments, the multivalent vaccine comprises live attenuated BRSV and live attenuated BRCV.

In yet other embodiments, the multivalent vaccine comprises live attenuated RVFV and live attenuated BVDV1. In still other embodiments, the multivalent vaccine comprises live attenuated RVFV and live attenuated BVDV2. In other embodiments, the multivalent vaccine comprises live attenuated RVFV and IBR. In still other embodiments, the multivalent vaccine comprises live attenuated RVFV and PI3. In yet other embodiments, the multivalent vaccine comprises live attenuated RVFV and live attenuated BRSV. In still other embodiments, the multivalent vaccine comprises live attenuated RVFV and live attenuated BRCV.

In related embodiments the multivalent vaccine comprises live attenuated BVDV1, live attenuated BVDV2, and live attenuated IBR virus. In still other embodiments the multivalent vaccine comprises live attenuated BVDV1, live attenuated BVDV2, and live attenuated PI3 virus. In yet other embodiments the multivalent vaccine comprises live attenuated BVDV1, live attenuated BVDV2, and live attenuated BRSV. In still other embodiments the multivalent vaccine comprises live attenuated BVDV1, live attenuated BVDV2, and live attenuated BRCV. In other embodiments the multivalent vaccine comprises live attenuated BVDV1, live attenuated IBR virus and live attenuated PI3 virus. In yet other embodiments the multivalent vaccine comprises live attenuated BVDV1, live attenuated IBR virus, and live attenuated BRSV. In still other embodiments the multivalent vaccine comprises live attenuated BVDV1, live attenuated IBR virus, and live attenuated BRCV. In still other embodiments the multivalent vaccine comprises live attenuated BVDV2, live attenuated IBR virus and live attenuated PI3 virus. In yet other embodiments the multivalent vaccine comprises live attenuated BVDV2, live attenuated IBR virus, and live attenuated BRSV. In still other embodiments the multivalent vaccine comprises live attenuated BVDV2, live attenuated IBR virus, and live attenuated BRCV. In yet other embodiments the multivalent vaccine comprises live attenuated BVDV1, live attenuated PI3 virus, and live attenuated BRSV.

In still other embodiments the multivalent vaccine comprises live attenuated BVDV1, live attenuated PI3 virus, and live attenuated BRCV. In yet other embodiments the multivalent vaccine comprises live attenuated BVDV2, live attenuated PI3 virus, and live attenuated BRSV. In still other embodiments the multivalent vaccine comprises live attenuated BVDV2, live attenuated PI3 virus, and live attenuated BRCV. In yet other embodiments the multivalent vaccine comprises live attenuated BVDV1, live attenuated BRSV, and live attenuated BRCV. In still other embodiments the multivalent vaccine comprises live attenuated BVDV2, live attenuated BRSV, and live attenuated BRCV.

In yet other embodiments, the multivalent vaccine comprises live attenuated IBR, live attenuated PI3, and live attenuated BRSV. In yet other embodiments, the multivalent vaccine comprises live attenuated IBR, live attenuated PI3, and live attenuated BRCV. In still other embodiments, the multivalent vaccine comprises live attenuated IBR, live attenuated BRSV, and live attenuated BRCV. In yet other embodiments, the multivalent vaccine comprises live attenuated PI3, live attenuated BRSV, and live attenuated BRCV.

In other embodiments the multivalent vaccine comprises live attenuated BVDV1, live attenuated BVDV2, live attenuated IBR virus, and live attenuated PI3 virus. In yet other embodiments the multivalent vaccine comprises live attenuated BVDV1, live attenuated BVDV2, live attenuated IBR virus, and live attenuated BRSV. In still other embodiments the multivalent vaccine comprises live attenuated BVDV1, live attenuated BVDV2, live attenuated IBR virus, and live attenuated BRCV. In yet other embodiments the multivalent vaccine comprises live attenuated BVDV1, live attenuated BVDV2, live attenuated PI3 virus, and live attenuated BRSV. In still other embodiments the multivalent vaccine comprises live attenuated BVDV1, live attenuated BVDV2, live attenuated PI3 virus, and live attenuated BRCV. In yet other embodiments the multivalent vaccine comprises live attenuated BVDV1, live attenuated BVDV2, live attenuated BRCV, and live attenuated BRCV.

In yet other embodiments the multivalent vaccine comprises live attenuated BVDV1, live attenuated IBR virus, live attenuated PI3 virus, and live attenuated BRSV. In still other embodiments the multivalent vaccine comprises BVDV1, live attenuated IBR virus, live attenuated PI3 virus, and live attenuated BRCV. In yet other embodiments the multivalent vaccine comprises BVDV1, live attenuated PI3 virus, live attenuated BRSV, and live attenuated BRCV. In still other embodiments the multivalent vaccine comprises live attenuated BVDV2, live attenuated IBR virus, live attenuated PI3 virus, and live attenuated BRSV. In still other embodiments the multivalent vaccine comprises BVDV2, live attenuated IBR virus, live attenuated PI3 virus, and live attenuated BRCV. In yet other embodiments the multivalent vaccine comprises BVDV2, live attenuated PI3 virus, live attenuated BRSV, and live attenuated BRCV. In yet other embodiments the multivalent vaccine comprises live attenuated IBR, live attenuated PI3 virus, live attenuated BRSV, and live attenuated BRCV.

In yet other embodiments the multivalent vaccine comprises live attenuated BVDV1, live attenuated BVDV2, live attenuated IBR virus, live attenuated PI3 virus, and live attenuated BRSV. In still other embodiments the multivalent vaccine comprises live attenuated BVDV1, live attenuated BVDV2, live attenuated IBR virus, live attenuated PI3 virus, and live attenuated BRCV. In yet other embodiments the multivalent vaccine comprises live attenuated BVDV1, live attenuated BVDV2, live attenuated IBR virus, live attenuated BRSV, and live attenuated BRCV. In still other embodiments the multivalent vaccine comprises live attenuated BVDV1, live attenuated BVDV2, live attenuated PI3 virus, live attenuated BRSV, and live attenuated BRCV. In yet other embodiments the multivalent vaccine comprises live attenuated BVDV1, live attenuated IBR virus, live attenuated PI3 virus, live attenuated BRSV, and live attenuated BRCV. In still other embodiments the multivalent vaccine comprises live attenuated BVDV2, live attenuated IBR virus, live attenuated PI3 virus, live attenuated BRSV, and live attenuated BRCV. In particular embodiments of this type, the multivalent vaccine comprises live attenuated BVDV1, live attenuated BVDV2, live attenuated PI3 virus, live attenuated IBR virus, live attenuated BRSV, and live attenuated BRCV.

The liquid stable vaccines of the present invention can further comprise a killed virus and/or a bacterium (e.g., a bacterin or an attenuated bacterium) and/or a sub-fraction of a bacterin. Accordingly, any of the liquid stable vaccines of the present invention that comprise one or more live virus vaccines can further comprise a killed virus and/or attenuated or killed bacterium and/or a sub-fraction of a bacterin, e.g., with one or more attenuated or killed bacterial antigens such as *Pasteurella multocida*, *Mannheimia haemolytica*, *Histophilus somni*, and *Mycoplasma bovis*.

The present invention further provides methods of aiding in the protection of a bovine against a clinical disease that arises from a bovine virus infection comprising administering a vaccine of the present invention to the animal. Accordingly, the present invention provides methods that comprise administering to a bovine any liquid stable vaccine of the present invention. In certain embodiments the administration is performed mucosally (e.g., by intranasal or oral route). In other embodiments the administration is performed parenterally. In still other embodiments the administration is performed intradermally. In yet other embodiments the administration is performed transdermally. In more specific embodiments, a vaccine of the present invention is administered to the animal subcutaneously. In other specific embodiments, a vaccine of the present invention is administered to the animal intramuscularly. The present invention also includes the use of primary and/or booster vaccines.

In particular embodiments, the method comprises administering to the bovine a liquid stable vaccine of the present invention that comprises a live attenuated virus. In certain embodiments the method of vaccinating a bovine is against a one or more viruses that include BVDV1, and/or BVDV2, and/or IBR, and/or PI3, and/or BRSV, and/or RVFV, and/or BRCV, and/or any combination thereof and against a bacterium against *Pasteurella multocida*, and/or *Mannheimia haemolytica*, and/or *Histophilus somni*, and/or *Mycoplasma bovis*, and/or any combination thereof, which comprises combining a liquid stable vaccine comprising BVDV1, and/or BVDV2, and/or IBR, and/or PI3, and/or BRSV, and/or RVFV, and/or BRCV, and/or any combination thereof, with a bacterial formulation comprising *Pasteurella multocida*, and/or *Mannheimia haemolytica*, and/or *Histophilus somni*, and/or *Mycoplasma bovis* and/or any combination thereof to form a combination vaccine and then administering the combination vaccine to the bovine.

In a specific embodiments the liquid stable vaccine comprises live attenuated BVDV1, live attenuated BVDV2, and live attenuated IBR virus. In other embodiments the liquid stable vaccine comprises live attenuated BVDV1, live attenuated BVDV2, live attenuated PI3 virus, and live attenuated BRSV. In still other embodiments, the liquid stable vaccine comprises live attenuated BVDV1, live attenuated BVDV2, live attenuated PI3 virus, live attenuated IBR virus, and live attenuated BRSV. In yet other embodiments, the liquid stable vaccine comprises live attenuated BVDV1, live attenuated BVDV2, live attenuated PI3 virus, live attenuated IBR virus, live attenuated BRSV, and live attenuated BRCV.

Any of the liquid stable, live, attenuated bovine virus vaccines of the present invention also can be combined with one or more attenuated or killed bacterial antigens such as *Pasteurella multocida, Mannheimia haemolytica, Histophilus somni*, and *Mycoplasma bovis*. In certain embodiments the bacterial antigen(s) is in a separate formulation, e.g., a vaccine, prior to being combined with the liquid stable, live, attenuated bovine virus vaccine of the present invention and the subsequent administration of the combined vaccine to the animal subject.

In a particular embodiment the liquid stable vaccine comprises live attenuated BVDV1, live attenuated BVDV2, live attenuated PI3 virus, live attenuated IBR virus, and live attenuated BRSV (plus or minus live attenuated BRCV) that is combined with live attenuated *Pasteurella multocida*, live attenuated *Mannheimia haemolytica*, and live attenuated *Histophilus somni*. In particular embodiments of this type, the liquid stable virus vaccine and live attenuated bacterial vaccine are stored in separate containers and combined prior to administration of the combined vaccine to the animal subject.

The present invention further provides kits that comprise a first container comprising a liquid stable, live, attenuated bovine virus vaccine of the present invention and a second container comprising a bovine bacterial vaccine. In one such embodiment the first container comprises a liquid stable, live, attenuated bovine virus vaccine that comprises one or more of a live attenuated BVDV1, a live attenuated BVDV2, a live attenuated PI3 virus, a live attenuated IBR virus, a live attenuated BRSV, a live attenuated RVFV, or a live attenuated BRCV and the second container comprises a bovine bacterial vaccine that comprises one or more of a *Pasteurella multocida*, a *Mannheimia haemolytica*, a *Mycoplasma bovis*, and a *Histophilus somni*. In certain embodiments, the bovine bacterial vaccine is stored as lyophilisate. In particular embodiments the bovine bacterial vaccine is a live bovine bacterial vaccine in which all of the bacterial antigens are live attenuated antigens. In other embodiments the bovine bacterial vaccine comprises at least one killed bacterial antigen. In a more particular embodiment of this type all of the bovine bacterial antigens are killed bacterial antigens. In certain embodiments the kit also contains instructions on how to store and/or combine and/or how to administer the vaccines in the kit.

Methods of making any and all of the liquid stable vaccines of the present invention are also provided. In certain embodiments the method comprises combining a therapeutically effective amount of a live attenuated virus with a 5-40% sugar additive, (e.g., a sugar alcohol or a combination of a sugar alcohol with a non-alcohol sugar), an amino acid, and a buffered solution at pH 6.0 to pH 8.0 to form a liquid stable vaccine. The amino acid can be arginine, glycine, glutamic acid, methionine, or combinations of arginine, glycine, glutamic acid and/or methionine. In particular embodiments the arginine and/or glycine and/or glutamic acid has a final concentration of 0.15 to 0.75 M in the liquid stable vaccine. In certain embodiments the vaccine further comprises methionine at a final concentration of 0.025 to 0.3 M in the liquid stable vaccine. In particular embodiments the therapeutically effective amount of a live attenuated virus is a therapeutically effective amount of a live attenuated bovine virus. In specific embodiments of this type, the therapeutically effective amount of a live attenuated bovine virus includes therapeutically effective amounts of live attenuated BVDV1, live attenuated BVDV2, live attenuated PI3 virus, live attenuated IBR virus and live attenuated BRSV. In a more particular embodiment of this type, the therapeutically effective amount of a live attenuated bovine virus includes therapeutically effective amounts of live attenuated BVDV1, live attenuated BVDV2, live attenuated PI3 virus, live attenuated IBR virus, live attenuated BRSV, and live attenuated BRCV.

The present invention further provides methods of storing any of the liquid stable bovine virus vaccines of the present invention for a time of 9 months, or 12 months, or 15 months, or 18 months, or 24 months, or 30 months, or even longer comprising taking a liquid stable bovine virus vaccine of the present invention and storing it at between about 0° C. to about 7° C. for 9 months, or 12 months, or 15 months, or 18 months, or 24 months, or 30 months, or even longer, with the liquid stable bovine virus vaccine remaining efficacious throughout the respective storing time of 9 months, or 12 months, or 15 months, or 18 months, or 24 months, or 30 months, or even longer.

These and other aspects of the present invention will be better appreciated by reference to the following Detailed Description.

DETAILED DESCRIPTION OF THE INVENTION

Because the liquid stable bovine virus vaccines of the present invention comprise live attenuated viruses, heretofore particular care would have been needed during the formulation of the vaccine to maintain the titer of the attenuated viruses at a level that is safely below that which can lead to a significant adverse event. Indeed, most live attenuated bovine virus vaccines are lyophilized, and lyophilization can lead to substantial declines in the efficacy of the attenuated live virus vaccines both due to the lyophilization process itself, as well as over time during long-term storage.

The present invention has overcome this problem by providing liquid stable bovine vaccines that remain efficacious, even during storage, without needing to increase the initial titer of the live attenuated viral antigen above a reliably safe level. As an additional benefit, the present invention provides a means for lowering the cost of manufacture of the vaccines provided by significantly reducing the amount of live attenuated bovine viruses necessary to make such a safe and efficacious vaccine. In addition, the live attenuated bovine virus vaccines of the present invention are more convenient to use than their lyophilized counterparts. Accordingly, the present invention provides safe and efficacious live attenuated bovine virus vaccines that can be stored as liquids at refrigerated temperatures and still remain stable for 12 to 18 months, and/or 18 to 24 months, and/or even longer.

Moreover surprisingly, the liquid stable live bovine virus vaccines of the present invention can include bovine viruses of any type. Thus, the liquid stable live virus vaccines of the present invention can include both enveloped and non-enveloped bovine viruses. In addition, the liquid stable live virus vaccines of the present invention can include live attenuated bovine viruses having single-stranded RNA genomes, single-stranded DNA genomes, or double-stranded DNA genomes. In addition, in particular cases, e.g., with the use of live attenuated RVFV, liquid stable live bovine virus vaccines can also be used for vaccinating sheep and goats.

The use of singular terms for convenience in the description is in no way intended to be so limiting. Thus, for example, reference to a "sugar additive" includes reference to one or more of such sugar additives, unless otherwise specified. The use of plural terms is also not intended to be limiting, unless otherwise specified. Similarly, a chemical compound that can be referred to as an acid or its corresponding base, unless otherwise specified, when denoted herein as either is intended to mean either form of the compound. Thus, the use of the term glutamic acid is meant to include glutamate and vice versa.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least one year when stored at or below 7° C. (e.g., in a standard refrigerator, and/or at 0° C.-7° C.). In particular embodiments a liquid stable vaccine remains efficacious when stored at or below 7° C. for at least 1.5 years. In more particular embodiments a liquid stable vaccine remains efficacious when stored at or below 7° C. for at least 2 years. In still more particular embodiments a liquid stable vaccine remains efficacious when stored at or below 7° C. for at least 2.5 to 3 years.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to bovine significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation. In one particular embodiment, high risk calves are light weight, commingled, long haul cattle with unknown health histories.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in bovine. In one such embodiment the bovine are at high risk of developing bovine respiratory disease. following commingling, transportation, changes in weather, changes in nutrition, and/or other stressors that can initiate a symptom and/or a disease related to the presence of the viral, bacterial, or parasitic pathogens commonly associated with bovine, targeted by the agent or combination of agents.

As used herein, the term "therapeutically effective amount" is an amount of a given antigen, e.g., a live attenuated bovine virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen. An "efficacious" vaccine retains sufficient titer for a given antigen to be compliant with the regulatory requirements for that antigen for the jurisdiction where the vaccine is administered, e.g., the administration of a vaccine in the United States is governed by the United States Department of Agriculture (USDA).

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous sugar, e.g., dextrose and/or glycerol solutions can be employed as carriers, particularly for injectable solutions. In addition, the carrier can be and/or comprise a hydrocolloid and/or polymer solution e.g., to thicken the bovine vaccines that are to be sprayed onto the cattle, e.g., calves.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein a "sugar additive" is a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol). Unless otherwise specifically stated to the contrary, the percent (%) of the sugar additive is provided as a weight (w) of the sugar additive to the volume (v) of the vaccine, (w/v) in the vaccine.

As used herein a "non-reducing sugar" is a sugar additive which in basic aqueous medium does not generate any compounds containing an aldehyde group. Examples of non-reducing sugars of the present invention include sucrose and trehalose.

As used herein, the terms "non-sugar alcohol" and "non-alcohol sugar" are used interchangeably. A sugar additive that is a "non-sugar alcohol" (or "non-alcohol sugar") as used herein, can be any sugar additive that is not a sugar alcohol, e.g., a non-reducing sugar.

As used herein, unless otherwise specifically stated to the contrary, the percent (%) of a solid additive, e.g., sugar additive or gelatin, in a vaccine is based on a 1% solution being 1 g of solid/100 ml of vaccine volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As used herein, the term, "approximately," is used interchangeably with the term "about" and generally signifies that a value is within twenty-five percent of the indicated value, unless otherwise indicated, e.g., a concentration of "about" 2 mM EDTA can be 1.5 mM to 2.5 mM EDTA.

As used herein, unless otherwise specifically stated to the contrary, the pH value provided is the pH value determined/measured at 25° C.

Because the liquid stable vaccines of the present invention ideally range in pH from pH 6.0 to pH 8.0, the liquid stable vaccines of the present invention can comprise a buffer. Buffers for use in the liquid stable vaccines of the present invention include but are not limited to: potassium phosphate, sodium phosphate, Tris, Tris-Histidine, BIS-Tris, BIS-Tris-Propane, sodium or potassium pyrophosphate, imidazole, PIPES, ACES, MOPS, MOPSO, BES, TES, tricine, glycylglycine, and HEPES. The buffers can be brought to the desired pH with the use of any suitable counterion.

The hydrolysate of whole casein that can be used in the liquid stable vaccines of the present invention can be obtained by a number of procedures including e.g., as an acid hydro lysate or an enzymatic hydrolysate. Such hydrolysates contain in the form of mixed amino acids and peptides having all of the amino acids originally present in casein. One pancreatic hydrolysate of whole casein that can be used in the liquid stable vaccines of the present invention is sold as CASEIN HYDROLYSATE ENZYMATIC® by MP Biomedicals. Comparable products are sold under the name of NZ-AMINE®, NZ-AMINE® A, NZ-AMINE® AS, and NZ-AMINE® B, and Tryptone by Sigma-Aldrich.

Examples of hydrocolloids that can be comprised by the vaccines of the present invention include: gelatin, starch polymers, and gums, such as xanthum gum, carragenin, and gum Arabic (*acacia* gum).

Multivalent Vaccines:

The present invention provides liquid stable multivalent vaccines. A liquid stable multivalent bovine vaccine of the present invention can include two or more antigens including one or more of the following live attenuated bovine viruses: BVDV1, BVDV2, PI3 virus, IBR virus, BRSV, RVFV, and/or BRCV. As noted above, a liquid stable multivalent bovine vaccine of the present invention can also include one or more of the following live attenuated viruses: BVDV1, BVDV2, PI3 virus, IBR virus, BRSV, RVFV, and/or BRCV, along with one or more killed bovine viruses.

In addition, a liquid stable, live, attenuated bovine virus vaccine of the present invention can include one or more live attenuated or killed bacterial antigens. In related embodiments, the liquid stable vaccine of the present invention can be combined with one or more live attenuated or killed bacterial antigens sometime prior to administration, but subsequent to storage. In specific embodiments of this type, the bacterial antigen(s) is comprised by a vaccine (either monovalent or multivalent) and that bovine bacterial vaccine is combined with a liquid stable live, attenuated bovine virus vaccine of the present invention prior to administration. In a more specific embodiment, the liquid stable, live, attenuated bovine virus vaccine can be used to liquefy/solubilize a freeze-dried bovine bacterial vaccine prior to the administration of the combined vaccine to the animal subject. In still other embodiments, the liquid stable, live, attenuated bovine virus vaccine and the attenuated and/or killed bovine bacterial vaccine are administered sequentially.

Accordingly, a liquid stable, live, attenuated bovine virus vaccine of the present invention can be combined with one or more live attenuated or killed bacterial vaccines comprising an antigen such as *Pasteurella multocida, Mannheimia haemolytica, Histophilus somni*, and *Mycoplasma bovis* prior to administration to the animal subject. Therefore, in certain embodiments the attenuated bacterial vaccine comprises an attenuated *Mannheimia hemolytica*. In particular embodiments of this type the attenuated *Mannheimia hemolytica* is a leukotoxin deletant. In a specific embodiment of this type, the attenuated *Mannheimia hemolytica* is an avirulent, live *Mannheimia haemolytica* in which the gene encoding leukotoxin A was modified to be missing the nucleotide sequence that encodes amino acids 34-378 of the leukotoxin A protein [see, U.S. Pat. No. 6,331,303 B1, hereby incorporated by reference in its entirety].

In yet other embodiments the attenuated bacterial vaccine comprises an attenuated *Pasteurella multocida*. In more particular embodiments the *Pasteurella multocida* comprises a deletion in its hyaE gene. In a specific embodiment of this type, the attenuated *Pasteurella multocida* is a live, avirulent, *Pasteurella multocida* in which the gene encoding the hyaE protein was modified to be missing the nucleotide sequence that encodes amino acids 239-359 of the hyaE protein, and/or missing nucleotides 718-1084 [see, U.S. Pat. No. 7,351,416 B2, hereby incorporated by reference in its entirety]. In yet other embodiments the attenuated bacterial vaccine comprises an attenuated *Histophilus somni*. In more particular embodiments the *Histophilus somni* is live, avirulent *Histophilus somni* that is an aroA mutant.

In particular embodiments of the methods of the present invention, the attenuated bacterial vaccine comprises both an attenuated *Mannheimia hemolytica* and an attenuated *Pasteurella multocida*. In a more specific embodiment, the antibacterial composition is an attenuated bacterial vaccine comprising an avirulent, live *Mannheimia haemolytica* in which the gene encoding leukotoxin A was modified to be missing the nucleotide sequence that encodes amino acids 34-378 of the leukotoxin A protein, and an avirulent, live *Pasteurella multocida* in which the gene encoding the hyaE protein was modified to be missing the nucleotide sequence that encodes amino acids 239-359 of the hyaE protein and/or missing nucleotides 718-1084. In more particular embodiments of the methods of the present invention, the attenuated bacterial vaccine comprises an attenuated *Mannheimia hemolytica*, an attenuated *Pasteurella multocida*, and an avirulent *Histophilus somni*.

Adjuvants:

As indicated above, the vaccines of the present invention also can include an adjuvant. In particular embodiments, the adjuvant comprises an aluminum salt. The use of aluminum salts in conjunction with live viral vaccines has been described. In particular embodiments the aluminum salt is chosen from the group consisting of aluminum phosphate, aluminum potassium phosphate, and aluminum hydroxide. Other well-known adjuvants include hydrocarbon oils and saponins One aluminum phosphate adjuvant is REHYDROPHOS® (General Chemical, Parsippany, N.J.). Examples of aluminum hydroxide adjuvants include: REHYDROGEL®, REHYDROGEL® HPA, or REHYDROGEL® LV (General Chemical, Parsippany, N.J.). Other well-known adjuvants include hydrocarbon oils, polymers, saponins and/or an adjuvant made up of gel particles of sodium acrylate in water, e.g., MONTANIDE™ PET GEL A™ (Seppic, Paris France). One low molecular weight copolymer adjuvant can form cross-linkage in solution to become a high molecular weight gel, e.g., POLYGEN™ (MVP Laboratories, Omaha). When added, the amount of adjuvant is usually between about 1% and 20% (v/v) in the vaccine. In particular embodiments the amount of adjuvant is between about 2% to 10% (v/v).

The vaccines of the present invention can also contain an anti-bacterial such as an antibiotic. Examples of such antibiotics can include: 10-100 μg/mL gentamicin, 0.5-5.0 μg/mL amphotericin B, 10-100 μg/mL tetracycline, 10-100 units/mL nystatin (mycostatin), 10-100 units/mL penicillin, 10-100 μg streptomycin, 10-100 μg polymyxin B, and 10-100 μg neomycin.

Vaccine Administration:

The liquid stable virus vaccines of the present invention may be administered by any conventional means, for example, by systemic administration, including by parenteral administration such as, without limitation, subcutaneous or intramuscular administration. The liquid stable virus vaccines of the present invention also may be administered by mucosal administration, such as by intranasal, oral, intratracheal, rectal, and/or ocular administration. Alternatively, the vaccines may be administered via a skin patch, in a delayed release implant, scarification, or topical administration. It is contemplated that a liquid stable virus vaccine of the present invention also may be administered via the drinking water and/or food of the recipient bovine.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

In certain embodiments of the methods of the present invention, a virus vaccine of the present invention that is suitable for mucosal administration comprises an attenuated IBR virus. In more particular embodiments the virus vaccine of the present invention that is suitable for mucosal administration comprises a live attenuated IBR virus, a live attenuated BVDV1, a live attenuated BVDV2, a live attenuated PI3 virus, and a live attenuated BRSV.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the species or breed (e.g., of a bovine), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL, and about 1.0 to 2.0 mL for intramuscular or subcutaneous administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose. In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The present invention may be better understood by reference to the following non-limiting Example, which is provided as exemplary of the invention. The following Example is presented in order to more fully illustrate embodiments of the invention. It should in no way be construed, however, as limiting the broad scope of the invention.

EXAMPLE

Example 1

Stability of Liquid Bovine Virus Vaccines

Introduction

Vaccines are critical for preventing diseases caused by pathogens in both humans and animals. Not surprisingly however, the focus on the type of vaccine employed in humans differs from that for animals. Thus, for humans, many vaccines are monovalent vaccines, i.e., containing a single immunizing agent that provides protection against a lone pathogen. On the other hand, multivalent vaccines are more prevalent in veterinary medicine. This is particularly true for vaccines employed in the cattle industry, e.g., by cattle producers for whom the cost of multiple vaccinations becomes a significant issue. Moreover, gathering cattle up for vaccination by running them through a restraining device and condensing animals in a small area within the close proximity of humans creates a stressful environment for the animals, which can often lead to the suppression of the immune system, inappetence, and/or physical injury to the cattle. Furthermore, each administration of a vaccine can potentially produce an effect on the local tissues that surround the corresponding injection site.

Accordingly, in verternary medicine it is often desirable to combine as many antigens as possible in a single multivalent vaccine. However, formulating such multivalent vaccines is not as straightforward as one might assume. For example, the vaccine antigens in a given formulation may prove to be incompatible. In addition, formulations that cause local tissue damage are generally not acceptable.

Moreover, vaccine formulations which may otherwise lead to liquid stability tend to have a higher content of dissolved solids. Vaccine formulations that have a higher solid content (in excess of 30 to 40%) are generally regarded as being hypertonic. Subcutaneous injection of a hypertonic solution can cause local swelling, edema, and possibly lead to tissue damage. Furthermore, even in the absence of tissue damage, the local swelling or edema at the injection site still can be visually undesirable to the customer. Hypertonic formulations do become less of an issue for the multivalent vaccines that are delivered intranasally or orally. However, a more desired formulation may still be the one that has a lower solid content because it generally correlates with a lower cost of goods.

Materials and Methods

Bulking Antigen Preparation:
Two sets of each viral antigen (BVDV1, BVDV2, PI3, and IBR) were produced. One set was grown in media free of animal origin, and the other set was grown in media containing components of animal origin. The data in Tables 2A and 2B below were obtained using viruses that were grown in media containing components of animal origin.
A. Stock Reagents:
  80% Sucrose 70% Sorbitol
  37.5% Trehalose 40% L-Arginine (from L-Arginine HCl)
  5% L-Methionine 1M Monopotassium Glutamic Acid
  10% Pluronic F-68 0.5M EDTA
  1M Potassium phosphate buffer
B. pH Adjustment: Bulk formulations are allowed to mix for 2-3 hours, then split: 3.5 L were allocated to 4° C. (low range) and 4.5 L to 25° C. (elevated range).

Low range: formulation was chilled to 4° C. (while mixing when possible) and the pH adjusted to 7.25. The formulation was then held overnight @ 4° C. and the pH was checked again the next morning to insure the pH has stabilized at 7.25. If a minor adjustment was necessary at any point the appropriate acid/base was used (K2HPO4 or KH2PO4).

Elevated range: formulation was warmed to 25° C. (while mixing when possible) and pH adjusted to 7.25. The formulation was then held overnight @ 25° C. and the pH was checked again the next morning to insure the pH had stabilized at 7.25. If a minor adjustment was necessary at any point the appropriate acid/base was used (K2HPO4 or KH2PO4). The pH drift between 15°, 25° and 37° C. is nominal, so the formulation was amped and store at each of the 3 temps.

pH meter: the pH is measured using a very sensitive pH probe and meter. The meter displays the pH to 3 significant figures to the right of the decimal. There is a separate temperature probe with meter and both must be in the solution and stable. The adjustment takes a good amount of time, the pH is critical to the experiment. This pH meter is capable of a 5 point calibration curve with 3 points being an absolute minimum.
C. Filter sterilize and sparge with Argon: Once the initial pH adjustment has been made all 7 formulations were filter sterilized using a 0.2 µM filter (preferred filter matrix=PES simply due to improved filter capacity). Currently filtration is performed using vacuum, a secondary benefit of vacuum filtering is the additional de-gassing of the formulation.

After the formulation has been filter sterilized it is sparged with argon gas to increase the depletion of $O_2$ which will hopefully yield lower reactivity of the formulation over time. Once sparge is complete ensure there is an argon overlay in place prior to storage (insure as tight a seal as possible for storage).
D. The morning after the formulation is prepared, the pH is confirmed/adjusted to 7.25 at the desired temperature (4° C. or 25° C.). If the formulation and previous procedures have been performed correctly the pH should be close to 7.25. With an overnight incubation the pH will have drifted slightly due to the completion of chemical reactions associated with the earlier pH adjustment and further de-gassing.

E. Thawing virus: Optimal conditions should be used in thawing the virus, usually quick thaw in a warm waterbath with frequent mixing to prevent the bulk liquid from warming, if thawing is necessary. The process is complete when there is a small amount of ice left in the formulation to keep things cold until it is ready for use and to remove residual heat from the liquid portion.

F. Adding virus to bulk formulations: Preparation of vaccine blend: 250 mL of 4° and 750 mL of 25° C. formulations are removed from bulks of each formulation (all 7 formulations) and put into an appropriate container (Nalgene screw cap bottles). When the virus is added in a very short time frame (a few minutes) then the virus may be added with no further issues. When the virus is not immediately added, an argon overlay should be put in place to displace residual $O_2$. Once the virus has been added a fresh argon overlay should be put into place prior to mixing. The argon gas should be added to the bottle using a low flowrate.

G. Filling the vaccines: Formulation Filling order: 4° C. formulation should always be filled before the 25° C. sister formulation.

Analytical Methods

All cell culture assays are performed in a clean cell environment. Manipulations, dilutions and media addition are done in a Class II biological safety cabinet under aseptic conditions. All plates, bottles, flasks, pipets, pipette tips and dilution tubes must be sterilized before use. All media and associated ingredients must be sterile.

BVDV1 Potency:

A suitable cell line for growth of BVDV is used for this titration assay. For example, Madin-Darby Bovine Kidney cells (MDBK) cells are grown to confluency in a flask or roller bottle using Hanks Modified Essential Media (HMEM) supplemented with 5-10% Fetal Bovine Sera (FBS), L-glutamine and an antibiotic (gentamicin (12-25 µg/mL)). The media is decanted from a flask/roller bottle of healthy growing MDBK cells approximately 24 hours before the desired time of viral titration. Rinse the serum containing media from the flask/roller bottle using Phosphate Buffered Saline, pH 7.2 (PBS). Decant and replace with a solution containing the appropriate amount of Trypsin/EDTA to gently loosen the cells from the surface of the flask/roller bottle. The amount of trypsin should be adjusted to the size of the flask or roller bottle surface. Place the flask/roller bottle containing the trypsinized cells into a 37 C incubator for enough time to allow the cells to detach. When the cells appear to be at the right level of detachment, add 5-20 mL of Eagles Modified Essential Media containing with L-glutamine and gentamicin (EMEM). 5% FBS is added to the EMEM to neutralize the trypsin. Pipet the cells to break up the clumps. Determine the cell density using a hemocytometer. The viability can be determined using a 4% solution of Trypan Blue. Dilute the cells to $1 \times 10^5$ cells per mL in EMEM with 5% FCS and add 100 µL to each well of a 96-well tissue culture plate. To prevent the media from evaporating, cover the plate and place cells in a humidified incubator set at 37 C with 5% $CO_2$. Prepare tubes to be used for the 10-fold dilutions for virus titration by adding the appropriate amount of EMEM/5% serum to each of the tubes. A separate tube is filled with EMEM for the negative control. Make the 10-fold dilutions of the virus sample into the prepared tubes. A prepared reference of Type 1 BVDV with known titer is also diluted in EMEM and used as a positive control. Ensure that the 96-well plate is confluent with a healthy monolayer of MDBK cells and apply 100 µL of each of the diluted virus samples to the appropriate wells of the 96-well MDBK cell plate. Include the negative and positive controls. Replace the lid on the plate and place in a humidified 37 C, 5% CO2 incubator for approximately 4 days. After 4 days, the plates may be read using an inverted microscope and examining the plate for cytopathic effect (CPE) of the virus on the cells. If the strain of BVDV is a non-cytopathic strain, the following procedure may be used to determine the virus titer. After 4 days, removed the infected plates from the incubator and decant the media into an appropriate waste container. Rinse the monolayer 2-times with PBS. After the second wash, remove the excess moisture by gently taping the plate against absorbent paper. Fix the cell substrates under a fume hood with 50-200 µL/well of cold 70% acetone/30% methanol fixative and allow the plate to fix at room temperature for 10 minutes. Decant the used fixative into an appropriate vessel. Remove excess moisture by gently tapping the plate against absorbent paper and allow the plate to air dry. The fixed plates may be stored at 2-7 C for up to 30 days before staining. To stain the plates, rinse each once with PBS and tap off the excess moisture. Add 50-75 uL per well of an antibody directed specifically towards a BVDV1. Replace the lid on the plates and incubate humidified at 37 C in 5% CO2 for 30-60 minutes. Remove the plates from the incubator and decant the fluid containing the unattached antibody. Rinse the plate at least 2× to remove the unbound antibody. Add 50-75 µL of fluorescent isothiocyanate tagged (FITC) secondary antibody diluted to the appropriate level to each well of the plate using a multichannel pipette. Replace the cover and incubate the plates in a humidified 37 C, 5% $CO_2$ incubator for approximately 30 minutes. Remove the plates from the incubator, remove the lid and decant the unbound FITC labeled antibody. Rinse the plates with PBS twice and tap the plates on absorbent paper to remove the excess moisture. The plates may be read immediately using a fluorescent microscope with the appropriate filters for the FITC conjugate. The infected substrate will contain cells with a cytoplasm that appears apple green and nuclei that are dark (unstained). For a cytopathic strain of BVDV1, consider wells showing obvious CPE as positive. All negative control wells should remain negative and not show CPE or stain positive. Calculate the virus titer by the Spearman-Karber method and report as the $\log_{10}$ $TCID_{50}$/mL. The test is valid if the negative controls are negative and the positive control falls within the expected range of titer for the sample.

BVDV2 Potency:

BVDV2 potency testing is done exactly the same as that for BVDV1. If the strain is a non-cytopathic strain, then an antibody directed against the type 2 strain should be used. The positive control virus will be BVDV2.

IBR Potency:

A suitable cell line for growth of IBR is used for this titration assay. For example, Madin-Darby Bovine Kidney cells (MDBK) cells are grown to confluency in a flask or roller bottle using Hanks Modified Essential Media (HMEM) supplemented with 5-10% Fetal Bovine Sera (FBS), L-glutamine and an antibiotic (gentamicin (12-25 µg/mL)). The media is decanted from a flask/roller bottle of healthy growing MDBK cells approximately 24 hours before the desired time of viral titration. Rinse the serum containing media from the flask/roller bottle using Phosphate Buffered Saline, pH 7.2 (PBS). Decant and replace with a solution containing the appropriate amount of Trypsin/EDTA to gently loosen the cells from the surface of the flask/roller bottle. The amount of trypsin should be adjusted to the size of the flask or roller bottle surface. Place the flask/roller bottle containing the trypsinized cells into a 37 C incubator for enough time to allow the cells to detach (5-10 minutes). When the cells appear to be at the right level of detachment, add 5-20 mL of Eagles Modified Essential Media containing with L-glutamine and gentamicin (EMEM). 5% FBS is added to the EMEM to neutralize the trypsin. Pipet the cells to break up the clumps. Determine the cell density using a hemocytometer. The viability can be determined using a 4% solution of Trypan Blue. Dilute the cells to $2.4 \times 10^5$ cells per mL in EMEM with 5% FCS and add 5 mL to each well of a 60 mm tissue culture plates. To prevent the media from evaporating, cover the plate and place cells in a humidified incubator set at 37 C with 5% $CO_2$. Prepare tubes to be used for the 10-fold dilutions for virus titration by adding the appropriate amount of EMEM/5% serum to each of the tubes. A separate tube is filled with EMEM for the negative control. Make the 10-fold dilutions of the virus sample into the prepared tubes. A prepared reference of IBR with known titer is also diluted in EMEM and used as a positive control. Ensure that the 60 mm plates are confluent with a healthy monolayer of MDBK cells. Label each plate with the sample identification and dilutions to be plated. The media is then decanted from each of the 60 mm plates. Inoculate each of the plates with 100 µL of sample to be tested, including the negative and positive controls. Tilt plates back and forth to distribute the inoculum. Replace the lid on the plate and place in a humidified 37 C, 5% CO2 incubator for approximately 60 minutes for absorption. Following absorption of the virus, add 5 mL of overlay medium consisting of Dulbecco's Minimal Essential Medium (DMEM), with 5% FCS, L-glutamine, gentamicin and carboxymethylcellulose to each 60 mm plate. After 4 days, decant the CMC overlay medium from each plate. Rinse each plate with water and decant. Add 2 mL (or enough to cover the bottom) of Crystal Violet stain to each plate or well, and incubate at room temperature (15-30° C.) for 20-30 minutes. Gently rinse the stain from each plate with cold water. Invert the plates and allow the plates to dry. After the plates have dried, visually count the plaques on the plates using an inverted microscope. Only use the dilutions that have average numbers of plaques between 10 and 150 to determine titer. Calculate the Plaque Forming Unit (PFU) virus titer/0.1 mL by the following calculation: PFU titer/0.1 mL=$Log_{10}$(average of plaques counted for each dilution of each individual titer)+$Log_{10}$(dilution factor). Report titers as $Log_{10}$) $TCID_{50}$/mL. The test is valid if the negative control shows no sign of plaques in the wells and the positive control titer is within the expected range.

BRSV Potency:

A suitable cell line for growth of BRSV is used for this titration assay. For example, Vero cells are grown in a flask or a roller bottle to confluency. The Vero cells can be grown on Dulbeccos modified essential media (DMEM), supplemented with antibiotics (gentamicin (12-50 µg/mL), fetal bovine sera (FBS 5%) and L-glutamine (2 mM). Titration plates are prepared approximately 24 hours before needed. The media is decanted from the healthy monolayer of Vero cells. The cells are rinsed with PBS. A small amount of trypsin/EDTA is added to the flask/roller bottle to loosen the cells from the surface. The flask/roller bottle is then incubated at 37 C for 5-10 minutes, at which time they are observed for detachment from the surface. Eagles modified essential media with antibiotics, L-glutamine, non-essential amino acids, lactalbumin hydrolysate (LAH 0.05%) and glucose (0.3%) is added to the flask (5-20 mL) containing trypsin/EDTA and the cells are pipetted to break up the clumps of cells. A hemocytometer is used to determine the number of cells, using a counter stain to determine the viability count for the cells. The cells are diluted to a final concentration of $1 \times 10^5$, using the EMEM as a diluent. Using a multichannel pipet, add 100 µL of the diluted cells to each well of a 96-well plate. Place the inoculated plates in a humidified incubator at 37 C, 5% $CO_2$ to allow the cells to attach and grow. Prepare tubes to be used for the 10-fold dilutions for virus titration by adding the appropriate amount of EMEM to each of the tubes. A separate tube is filled with EMEM for the negative control. Make the 10-fold dilutions of the virus sample into the prepared tubes. A prepared reference of BRSV with known titer is also diluted in EMEM and used as a positive control.

Ensure that the 96-well plate is confluent with a healthy monolayer of Vero cells and apply 100 µL of each of the diluted virus samples to the appropriate wells of the 96-well Vero cell plate. Include the negative and positive controls. Replace the lid on the plate and place in a humidified 37 C, 5% CO2 incubator for approximately 8 days before evaluation. On the eight day, an inverted microscope is used to evaluate each well of the 96-well plate for cytopathic effect (CPE). The negative control is viewed first to determine the amount of background debris that is the baseline for each well. Record the number of CPE positive wells for each dilution. Calculate the virus titer by using the Spearman-Karber method and report as $Log_{10}$ $TCID_{50}$/mL. The test is valid if the negative control shows no sign of CPE in the wells and the positive control titer is within the expected range.

PI3 Potency:

A suitable cell line for growth of PI3 is used for this titration assay. For example, Vero cells are grown in a flask or a roller bottle to confluency. The Vero cells can be grown on Dulbeccos modified essential media (DMEM), supplemented with antibiotics (gentamicin (12-50 µg/mL), fetal bovine sera (FBS 5%) and L-glutamine (2 mM). The media is decanted from the healthy monolayer of Vero cells. The cells are rinsed with PBS. A small amount of trypsin/EDTA is added to the flask/roller bottle to loosen the cells from the surface. The flask/roller bottle is then incubated at 37 C for 5-10 minutes, at which time they are observed for detachment from the surface. Eagles modified essential media with gentamicin, L-glutamine and 5% FCS is added to the flask (5-20 mL) containing trypsin/EDTA and the cells are pipetted to break up the clumps of cells. A hemocytometer is used to determine the number of cells, using a counter stain (Trypan Blue) to determine the viability count for the cells. The cells are diluted to a final concentration of $1 \times 10^5$, using the EMEM as a diluent. Using a multichannel pipet, add 100 µL of the diluted cells to each well of a 96-well plate.

Place the inoculated plates in a humidified incubator at 37 C, 5% $CO_2$ to allow the cells to attach and grow. Prepare tubes to be used for the 10-fold dilutions for virus titration by adding the appropriate amount of EMEM to each of the tubes. A separate tube is filled with EMEM for the negative control. Make the 10-fold dilutions of the virus sample into the prepared tubes. A prepared reference of PI3 with known titer is also diluted in EMEM and used as a positive control. Ensure that the 96-well plate is confluent with a healthy monolayer of Vero cells and apply 100 µL of each of the diluted virus samples to the appropriate wells of the 96-well Vero cell plate. Include the negative and positive controls. Replace the lid on the plate and place in a humidified 37 C, 5% CO2 incubator for approximately 7 days before evaluation. On the seventh day, an inverted microscope is used to evaluate each well of the 96-well plate for cytopathic effect (CPE). The negative control is viewed first to determine the amount of background debris that is the baseline for each well. Record the number of CPE positive wells for each dilution. Calculate the virus titer by using the Spearman Karber method and report as $Log_{10}$ $TCID_{50}$/mL. The test is valid if the negative control shows no sign of CPE in the wells and the positive control titer is within the expected range.

BRCV Potency:

MDBK cells are grown using DMEM with L-glutamine, fetal bovine sera and antibiotics (Growth Media) in a flask or roller bottle until a confluent monolayer of health cells is achieved. Decant the flask/bottle and rinse with phosphate buffered saline (PBS). Decant the PBS and add sufficient trypsin containing solution to detach cells from the surface. Place the culture back in a 37 C incubator to give the cells time to detach. Once the cells detach from the surface, add an amount of media equivalent to 2× the amount of trypsin used is added to the cells. The cells are pipetted several times to break up the clumps of cells. A viable count is performed using a hemocytometer or other suitable method, using Trypan blue to determine the percentage of non-viable cells in the suspension. The cell suspension is then diluted with the Growth Media to $2×10^5$ cells/ml. Using a multichannel pipettor, 100 µl, of the cell suspension is added to each well of a 96 well tissue culture plate. The seeded plates are incubated in at 37 C, 5% $CO_2$, high humidity until a monolayer is formed at about 90-100% confluency. Samples containing live viruses are diluted 10-fold in Inoculation Media (DMEM, L-glutamine, antibiotics and Type IX trypsin). BRCV is a trypsin dependent virus and thus trypsin must be added to the inoculation media in order for the viruses to infect the cells. FBS must not be added to the dilution media for trypsin dependent viruses. When the 96 well plates are ready, decant the Growth Media and wash the plate with PBS. Remove the PBS from the 96 well plate containing the MDBK monolayer of cells and immediately apply the diluted samples of virus to the plate. A dilution series of a positive control containing a known amount of virus is also added to the plate. A negative control series containing only media is also added to the plate. Incubate the plates at 37 C, 5% $CO_2$ for five days. After 5 days, remove the plates from the incubator and observe cells, using a microscope, for the cytopathic effect of the virus (CPE). Wells showing CPE are marked as positive, wells with intact cells are considered negative. Calculate the titers of the positive control and the samples by the Spearman-Karber method and report as $TCID_{50}$/ml. The assay is valid if the negative control wells show no sign of cytopathic effect and the positive control falls within the expected range.

RESULTS/CONCLUSION

Stabilizer formulations for bovine virus vaccines were prepared, and then sparged using argon gas, filter sterilized using 0.2 um PES bottle top filters and an argon gas overlay was applied prior to storage. On the day of fill the virus was added and mixed, the vaccine was then dispensed 1 mL in a 2.2 mL glass ampule, back-filled with argon gas, flame sealed and incubated. Monovalent vaccines of BRSV, BVDV1 and IBR were generated for each stabilizer combination and incubated at either 15° C. or 25° C. PI3 was left out because earlier results indicated that this virus behaved similarly to BRSV. This preliminary experiment surprisingly showed that improved levels of success could be obtained using a combination of sorbitol and arginine, as well as a tendency for more simplistic stabilizers to perform better across the range of the viruses tested.

Next, an accelerated (25° C.) and real time (4° C.) stability study was set up to compare multiple formulations in view of the excipient screening detailed above (see, Table 1). Stabilizer formulations were prepared, then sparged using argon gas, filter sterilized using 0.2 um PES bottle top filters and an argon gas overlay was applied prior to storage. On the day of fill the virus was added and mixed, the vaccine was then dispensed 1 mL in a 2.2 mL glass ampule, back-filled with argon gas, flame sealed and incubated. Combination samples were also filled ~10 mL into glass and plastic vaccine vials, overlayed with argon gas, stoppered and crimp sealed.

In all, eleven different formulations proved to be potential candidates for liquid stable formulations of a multivalent cattle vaccine (Table 1). Real time studies, e.g., at 4° C., were performed on multivalent vaccine formulations comprising BVDV1, BVDV2, IBR, PI3, and BRSV, and monovalent vaccine formulations of BRCV. The results of these studies are provided in Tables 2A and 2B below.

Stability testing was completed at three month intervals. At nine months, an assessment was made on the formulations to narrow the study. The most difficult vaccine antigens to stabilize appeared to be BVDV1 and IBR. Discontinuation of the study of a given formulation was based, at least in part on those that: had lost more than one log in titer for any of the 5 vaccine antigens at 9 months; had equivalent results to another formulation and had the same ingredients, but in higher concentrations; and/or had the same formulations, but had additional ingredients which didn't appear to have any affect. Any formulation that had a sudden drop in titer at one timepoint was carried on for an additional time point to determine if it was an actual instability or the variability in the assay (unless it met any of the exclusion criteria above).

TABLE 1

| | | | | Formulations (final concentrations of reagents) | | | | | | |
|---|---|---|---|---|---|---|---|---|---|---|
| Formulation | Sucrose | Trehalose | Sorbitol | L-Arginine | L-Methionine | Glutamic acid | Pluronic F-68 | EDTA | K-phos Buffer | pH |
| 6-1 | 30% | | | 8% (0.46M) | | | | | 11 mM | 7.2 |
| 6-2 | 30% | | | 0.46M | 1% | | | | 11 mM | 7.2 |
| 6-3 | | | 15% | 0.46M | | | | | 11 mM | 7.2 |
| 6-4 | | | 15% | 5.2% (0.3M) | | | | | 11 mM | 7.2 |
| 6-5 | | | 15% | 3% (0.173M) | | | | | 11 mM | 7.2 |
| 6-6 | 10% | | 15% | 0.46M | | | | | 11 mM | 7.2 |
| 6-7 | | 10% | 15% | 0.46M | | | | | 11 mM | 7.2 |
| 6-8 | | | 15% | 0.46M | | | 1.5% | 0.5 mM | 11 mM | 7.2 |
| 6-9 | | | 23% | 0.46M | | | | | 11 mM | 7.2 |
| 6-10 | | 23% | | 0.46M | | | | | 11 mM | 7.2 |
| 6-11 | | | 15% | 0.25M | | 0.25M | | | 11 mM | 7.2 |

TABLE 2A

Relative Stability of Antigens Based upon 15 Months of Storage at 4° C.

| Blend | Titer (Log10 TCID50) of each virus fraction during storage at 4° C. (months) BVDV1 | | | | | | BVDV2 | | | | | | IBR | | | | | | Overall Ranking |
|---|---|---|---|---|---|---|---|---|---|---|---|---|---|---|---|---|---|---|---|
| 6-1 | 6.3 | 6.0 | 5.7 | 6.1 | 5.6 | 5.3 | 6.5 | 5.8 | 5.7 | 5.2 | 5.5 | 5.0 | 5.2 | 4.8 | 4.5 | 3.8 | 3.9 | 3.8 | + |
| 6.2 | 6.5 | 6.4 | 5.6 | 5.8 | ND | ND | 6.1 | 5.6 | 5.8 | 5.6 | ND | ND | 5.0 | 4.8 | 4.5 | 3.7 | ND | ND | + |
| 6-3 | 6.7 | 6.4 | 6.2 | 5.8 | 5.5 | 5.6 | 6.0 | 5.6 | 6.0 | 5.7 | 5.4 | 4.9 | 5.1 | 4.9 | 4.5 | 4.2 | 4.1 | 4.1 | ++ |
| 6-4 | 6.2 | 6.3 | 5.9 | 5.7 | 5.7 | 5.6 | 6.0 | 5.7 | 5.7 | 5.3 | 5.9 | 5.0 | 5.3 | 5.1 | 5.3 | 4.7 | 4.3 | 4.4 | +++++ |
| 6-5 | 6.0 | 6.2 | 5.6 | 5.8 | 5.7 | 5.3 | 5.9 | 5.6 | 6.0 | 5.7 | 5.3 | 5.3 | 5.3 | 5.5 | 4.9 | 4.4 | 4.5 | 4.4 | +++ |
| 6-6 | 6.3 | 6.2 | 6.0 | 5.5 | 5.5 | 5.2 | 5.7 | 5.6 | 5.6 | 5.4 | 5.0 | 4.7 | 4.9 | 4.5 | 4.7 | 4.0 | 4.5 | 4.2 | +++ |
| 6-7 | 6.2 | 6.1 | 5.9 | 5.7 | ND | ND | 6.5 | 5.6 | 5.7 | 5.2 | ND | ND | 5.1 | 4.6 | 4.8 | 4.6 | ND | ND | + |
| 6-8 | 6.0 | 6.4 | 5.5 | 5.6 | ND | ND | 6.5 | 6.1 | 5.6 | 5.0 | ND | ND | 5.3 | 4.6 | 4.8 | 4.2 | ND | ND | + |
| 6-9 | 6.0 | 5.7 | 5.4 | 4.5 | ND | ND | 6.1 | 5.7 | 5.3 | 4.9 | ND | ND | 4.8 | 4.6 | 4.9 | 4.5 | ND | ND | + |
| 6-10 | 6.1 | 5.8 | 5.6 | 5.3 | ND | ND | 6.3 | 5.7 | 5.2 | 4.8 | ND | ND | 5.2 | 4.5 | 4.6 | 4.0 | ND | ND | + |
| 6-11 | 6.0 | 6.3 | 6.0 | 4.9 | 5.6 | 5.0 | 6.0 | 5.6 | 5.8 | 4.8 | 5.2 | 4.9 | 5.0 | 5.1 | 5.3 | 4.7 | 4.9 | 4.6 | +++++ |
| Months | 0 | 3 | 6 | 9 | 12 | 15 | 0 | 3 | 6 | 9 | 12 | 15 | 0 | 3 | 6 | 9 | 12 | 15 | |
| Minimum Expiration Titer | | | | | | 3.8 | | | | | | 3.5 | | | | | | 3.6 | |

ND = Not done -titration was stopped for reasons provided above.

1 - The minimum expiration titer is the product specification at the end of shelf life.

2 - Time "0" titer is from the blend immediately after mixing and preparation of the vaccine mixture.

3 - Overall Ranking is based upon the formulation which does the best job of stabilizing all six viruses and is designated by: "+" as being the least favorable to "+++++" as being the most favorable.

TABLE 2B

Relative Stability of Antigens Based upon 15 Months of Storage at 4° C.

| Blend | Titer (Log10 TCID50) of each virus fraction during storage at 4° C. (months) RBCV* | | | | | | PI3 | | | | | | BRSV | | | | | | Overall Ranking |
|---|---|---|---|---|---|---|---|---|---|---|---|---|---|---|---|---|---|---|---|
| 6-1 | 7.2 | 5.9 | 6.5 | 6.3 | | | 7.1 | 6.6 | 6.7 | 6.9 | 6.6 | 6.8 | 5.1 | 5.3 | 3.5 | 5.3 | 5.4 | 5.3 | + |
| 6.2 | Formulation Not Tested | | | | | | 6.7 | 6.8 | 6.7 | 6.8 | ND | ND | 5.3 | 5.3 | 5.0 | 5.3 | ND | ND | + |
| 6-3 | 7.2 | 5.9 | 6.2 | 6.3 | | | 7.1 | 6.7 | 6.8 | 7.2 | 6.4 | 6.8 | 5.4 | 4.6 | 4.9 | 4.9 | 5.5 | 4.8 | ++ |
| 6-4 | 7.1 | 5.8 | 6.2 | 6.3 | | | 6.8 | 6.7 | 6.8 | 6.9 | 6.6 | 6.5 | 5.0 | 5.0 | 5.0 | 5.0 | 5.1 | 4.8 | +++++ |
| 6-5 | 7.4 | 5.8 | 5.7 | 5.5 | | | 6.6 | 7.1 | 6.8 | 6.5 | 6.7 | 6.3 | 5.6 | 5.3 | 5.0 | 3.7 | 5.2 | 4.5 | +++ |
| 6-6 | 7.3 | 6.1 | 5.8 | 6.2 | | | 6.8 | 6.8 | 7.1 | 6.4 | 6.8 | 6.7 | 5.7 | 5.5 | 5.2 | 5.1 | 5.5 | 4.7 | +++ |
| 6-7 | Formulation Not Tested | | | | | | 6.8 | 6.8 | 6.8 | 7.0 | ND | ND | 5.1 | 4.7 | 3.5 | 5.2 | ND | ND | + |
| 6-8 | Formulation Not Tested | | | | | | 7.0 | 6.6 | 6.4 | 6.4 | ND | ND | 5.4 | 4.6 | 5.1 | 5.3 | ND | ND | + |
| 6-9 | 7.4 | 6.1 | 5.5 | 6.3 | | | 6.8 | 6.7 | 6.8 | 6.7 | ND | ND | 4.3 | 5.5 | 5.1 | 3.5 | ND | ND | + |
| 6-10 | Formulation Not Tested | | | | | | 6.8 | 6.8 | 6.4 | 6.6 | ND | ND | 4.9 | 5.3 | 4.9 | 4.6 | ND | ND | + |
| 6-11 | Formulation Not Tested | | | | | | 7.1 | 6.6 | 5.8 | 6.4 | 6.4 | 6.4 | 5.4 | 5.1 | 5.0 | 5.3 | 5.6 | 5.2 | +++++ |
| Months | 0 | 3 | 6 | 9 | 12 | 15 | 0 | 3 | 6 | 9 | 12 | 15 | 0 | 3 | 6 | 9 | 12 | 15 | |
| Minimum Expiration Titer | | | | | | 5.7 | | | | | | 5.1 | | | | | | 3.8 | |

*There is a potential issue with Day 0 titers for RBCV, results appear to be a log too high. 9 months of testing on RBCV, some formulations were not evaluated for RBCV.

ND = Not done -titration was stopped for reasons provided above.

1 - The minimum expiration titer is the product specification at the end of shelf life.

2 - Time "0" titer is from the blend immediately after mixing and preparation of the vaccine mixture.

3 - Overall Ranking is based upon the formulation which does the best job of stabilizing all six viruses and is designated by: "+" as being the least favorable to "+++++" as being the most favorable.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A liquid stable vaccine that comprises a live attenuated bovine respiratory coronavirus (BRCV), a 5-40% (w/v) sugar alcohol, and 0.15 to 0.75 M of an amino acid selected from the group consisting of arginine, glutamic acid, glycine, and any combination thereof; wherein the liquid stable vaccine has a pH of 6.0 to 8.0.

2. The liquid stable vaccine of claim 1 wherein the sugar alcohol is sorbitol.

3. The liquid stable vaccine of claim 2 wherein the amino acid is arginine.

4. The liquid stable vaccine of claim 3, further comprising a live attenuated bovine virus is selected from the group consisting of a bovine viral diarrhea virus (BVDV), infectious bovine rinotracheitis virus (IBR), parainfluenza type 3 virus (PI3), bovine respiratory syncytial virus (BRSV), and any combination thereof; and wherein the live attenuated BVDV is selected from the group consisting of BVDV1, BVDV2, and BVDV1 and BVDV2.

5. The liquid stable vaccine of claim 3 that further comprises a killed bovine virus.

6. The liquid stable vaccine of claim 3 that further comprises a bacterium.

7. The liquid stable vaccine of claim 6 wherein the bacterium is selected from the group consisting of a live attenuated *Pasteurella multocida*, a live attenuated *Mannheimia haemolytica*, a live attenuated *Histophilus somni*, a live attenuated *Mycoplasma bovis*, a killed *Pasteurella multocida*, a killed *Mannheimia haemolytica*, a killed *Histophilus somni*, a killed *Mycoplasma bovis*, and any combination thereof.

8. The liquid stable vaccine of claim 1 further comprising a sugar additive that is a non-alcohol sugar, wherein the total amount of the sugar alcohol and the non-alcohol sugar in the liquid stable vaccine is 10-40% (w/v).

9. The liquid stable vaccine of claim 1 wherein the non-alcohol sugar is selected form the group consisting of sucrose and trehalose.

10. The liquid stable vaccine of claim 1 that further comprises a component selected from the group consisting of an antioxidant, a surfactant, and a chelator.

11. The liquid stable vaccine of claim 1 that further comprises a buffer.

12. The liquid stable vaccine of claim 11 wherein the buffer comprises 2.5 to 50 mM potassium phosphate.

13. The liquid stable vaccine of claim 1, wherein the amino acid is arginine.

14. The liquid stable vaccine of claim 13, further comprising a live attenuated bovine viral diarrhea virus (BVDV), and a live attenuated infectious bovine rinotracheitis virus (IBR); and wherein the live attenuated BVDV is selected from the group consisting of BVDV1, BVDV2, and BVDV1 and BVDV2.

15. The liquid stable vaccine of claim 14, that further comprises, a live attenuated PI3 and a live attenuated BRSV.

16. A method of vaccinating a bovine against bovine viral diarrhea virus (BVDV), infectious bovine rinotracheitis (IBR) virus, parainfluenza type 3 (PI3), bovine respiratory syncytial virus (BRSV), and bovine respiratory coronavirus (BRCV) comprising administering to the bovine the liquid stable vaccine of claim 15.

17. The method of claim 16, wherein said administering is performed by subcutaneous injection.

18. A method of vaccinating a bovine against bovine respiratory coronavirus (BRCV) comprising administering to the bovine the liquid stable vaccine of claim 1.

19. The method of claim 18, wherein said administering is performed by subcutaneous injection.

20. A method of making a liquid stable vaccine that comprises combining a therapeutically effective amount of a live attenuated bovine respiratory coronavirus (BRCV) with a 5-40% (w/v) sugar alcohol, and 0.15 to 0.75 M arginine; wherein the liquid stable vaccine has a pH of 6.0 to 8.0.

* * * * *

UNITED STATES PATENT AND TRADEMARK OFFICE
CERTIFICATE OF CORRECTION

PATENT NO.        : 9,603,924 B2
APPLICATION NO.   : 14/775003
DATED             : March 28, 2017
INVENTOR(S)       : Brad Eddy et al.

It is certified that error appears in the above-identified patent and that said Letters Patent is hereby corrected as shown below:

On the Title Page

Under item (71) Applicants:
Delete: "INTERVET INTERNATIONAL B.V., Boxmeer (NL);"

Signed and Sealed this
Fifth Day of December, 2017

Joseph Matal
*Performing the Functions and Duties of the
Under Secretary of Commerce for Intellectual Property and
Director of the United States Patent and Trademark Office*